United States Patent [19]
Galt et al.

[11] 4,001,418
[45] Jan. 4, 1977

[54] 1'-SUBSTITUTED-THIOXANTHENE-9-SPIRO-4'-PIPERIDINE DERIVATIVES AND THE 10-OXIDES AND 10,10-DIOXIDES THEREOF

[75] Inventors: Ronald Hilson Begg Galt; Edwin Harry Paterson Young, both of Macclesfield, England

[73] Assignee: Imperial Chemical Industries Limited, London, England

[22] Filed: Jan. 9, 1975

[21] Appl. No.: 539,627

[30] Foreign Application Priority Data

Feb. 4, 1974 United Kingdom ............... 5017/74

[52] U.S. Cl. ........................ 424/267; 260/293.57; 260/328
[51] Int. Cl.² ..................................... C07D 409/04
[58] Field of Search ............... 260/293.57; 424/267

[56] References Cited

UNITED STATES PATENTS

| | | | |
|---|---|---|---|
| 2,368,006 | 1/1945 | Cusic | 260/293.57 |
| 3,048,595 | 8/1962 | Zirkle et al. | 260/293.57 |
| 3,275,640 | 9/1966 | Engelhardt et al. | 260/293.57 |
| 3,408,355 | 10/1968 | Renz et al. | 260/293.57 |
| 3,470,188 | 9/1969 | Kaiser et al. | 260/293.57 |
| 3,721,672 | 3/1973 | Muller-Calgan et al. | 260/293.57 |

*Primary Examiner*—Natalie Trousof
*Attorney, Agent, or Firm*—Cushman, Darby & Cushman

[57] ABSTRACT

The disclosure relates to thioxanthene derivatives which possess analgesic activity, to processes for the manufacture of said derivatives and to pharmaceutical compositions containing them. Typical of the thioxanthene derivatives disclosed is 4-acetoxy-6-chloro-1'-methylthioxanthene-9-spiro-4'-piperidine.

10 Claims, No Drawings

1'-SUBSTITUTED-THIOXANTHENE-9-SPIRO-4'-PIPERIDINE DERIVATIVES AND THE 10-OXIDES AND 10,10-DIOXIDES THEREOF

This invention relates to thioxanthene derivatives which possess analgesic properties.

According to the invention there is provided a thioxanthene derivative of the formula:

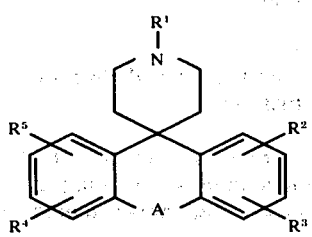

wherein $R^1$ stands for
1. a hydrogen atom or
2. an alkyl radical of 1 to 10 carbon atoms;
3. an alkenyl radical of 3 to 10 carbon atoms;
4. a cycloalkylalkyl radical of 4 to 7 carbon atoms optionally substituted in the cycloalkyl nucleus by an aryl radical of 6 to 10 carbon atoms or by one or two alkyl radicals of 1 to 3 carbon atoms;
5. an aroylalkyl radical of 8 to 12 carbon atoms optionally substituted in the aryl nucleus by one to three halogen atoms or alkyl radicals of 1 to 3 carbon atoms; or
6. a hydroxyalkyl radical of 2 to 5 carbon atoms;

$R^2$, $R^3$, $R^4$ and $R^5$, which may be the same or different, stand for
7. hydrogen atoms or
8. halogen atoms; or
9. alkyl radicals of 1 to 5 carbon atoms;
10. haloalkyl radicals of 1 to 5 carbon atoms;
11. alkoxy radicals of 1 to 5 carbon atoms;
12. alkylthio radicals of 1 to 5 carbon atoms;
13. alkanoyloxy radicals of 1 to 5 carbon atoms;
14. hydroxyalkyl radicals of 1 to 5 carbon atoms; or
15. hydroxy radicals;

A stands for a sulphur atom or for a sulphinyl or sulphonyl radical; and the pharmaceutically-acceptable acid-addition salts thereof.

It is to be understood that when $R^1$ is an alkenyl radical, the double bond it contains is separated from the nitrogen atom of the spiropiperidine ring by at least one carbon atom and when $R^1$ is a hydroxyalkyl radical, the oxygen atom it contains is separated from the nitrogen atom of the spiropiperidine ring by at least two carbon atoms.

The numbering system used in this specification to describe the position of a substituent on the thioxanthene nucleus is as follows:

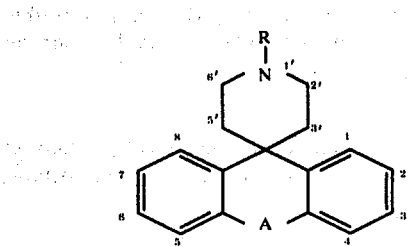

Reference to substitution at a particular position means substitution at that numbered position in the thioxanthene nucleus as defined immediately above.

A particular value for A is a sulphur atom or sulphinyl radical.

A particular value for $R^1$ when it is an alkyl radical is such a radical of 1 to 8 carbon atoms, for example a methyl, ethyl, n-propyl, i-propyl, n-butyl, n-pentyl or n-hexyl radical.

A particular value for $R^1$ when it is an alkenyl radical is such a radical of 3 to 7 carbon atoms for example an allyl or 3-methylbut-2-enyl radical.

A particular value for $R^1$ when it is a cycloalkylalkyl or hydroxyalkyl radical is a cyclopropylmethyl, cyclobutylmethyl or 2-hydroxyethyl radical.

A particular value for $R^2$, $R^3$, $R^4$ or $R^5$ when it is a halogen atom is a fluorine or chlorine atom and more particularly a chlorine atom.

A particular value for $R^2$, $R^3$, $R^4$ or $R^5$ when it is an alkyl, haloalkyl, alkoxy, alkylthio, alkanoyloxy or hydroxyalkyl radical is such a radical of 1 to 3 carbon atoms, for example a methyl, trifluoromethyl, methoxy, methylthio, acetoxy or 1-hydroxyethyl radical, and more particularly a methoxy or acetoxy radical.

A particular group of compounds of the invention, is that wherein when $R^2$ and $R^3$ are both other than hydrogen atoms they are the same and when $R^3$ and $R^4$ are both other than hydrogen atoms they are the same.

Further particular groups of compounds of the invention, in which each substitutent is described by number as defined above and A can either be S, SO or $SO_2$ or A can be S or SO, are as follows:

$R^1 = 1$ or 2
$R^2 = 11, 12, 13$ or 15 substituted at the 4-position
$R^3, R^4, R^5 = 7$ $R^1 = 1$ or 2
$R^2 = $ hydroxy, methoxy or acetoxy substituted at the 4-position
$R^3, R^4, R^5 = 7$ $R^1 = $ hydrogen or methyl
$R^2 = 11, 12, 13$ or 15 substituted at the 4-position
$R^3, R^4, R^5 = 7$ $R^1 = $ hydrogen or methyl
$R^2 = $ hydroxy, methoxy or acetoxy substituted at the 4-position
$R^3, R^4, R^5 = 7$ $R^1 = 1, 2, 3, 4, 5$ or 6
$R^2 = 8, 9, 10, 11, 12$ or 14 substituted at the 2- or 3-position
$R^3, R^4 R^5 = 7$ $R^1 = 2, 3, 4, 5$ or 6
$R^2 = $ chlorine, bromine, methyl, trifluoromethyl, methoxy, methylthio or 1-hydroxyethyl substituted at the 2-or 3-position
$R^3, R^4, R^5 = 7$
$R^1 = 2$ or 5

$R^2$ = chlorine, bromine, methyl, trifluoromethyl, methoxy, methylthio or 1-hydroxyethyl substituted at the 2-or 3-position
$R^3$, $R^4$, $R^5$ = 7
$R^1$ = methyl
$R^2$ = chlorine, bromine, methyl, trifluoromethyl, methoxy, methylthio or 1-hydroxyethyl substituted at the 2-or 3-position
$R^3$, $R^4$, $R^5$ = 7
$R^1$ = 1, 2, 3, 4, 5 or 6
$R^2$ = 11, 12, 13 or 15 substituted at the 4-position
$R^4$ = 8, 9, 10, 11, 12 or 15 substituted at the 6-, 7- or 8-position
$R^3$, $R^5$ = 7
$R^1$ = 1, 2, 3, 4, 5 or 6
$R^2$ = hydroxy, methoxy or acetoxy substituted at the 4-position
$R^4$ = 8, 9, 10, 11, 12 or 15 substituted at the 6-, 7- or 8-position
$R^3$, $R^5$ = 7
$R^1$ = 1, 2, 3, 4, 5 or 6
$R^2$ = 11, 12, 13 or 15 substituted at the 4-position
$R^4$ = fluorine, chlorine, methyl, trifluoromethyl, methoxy, methylthio or hydroxy substituted at the 6-, 7- or 8-position
$R^3$, $R^5$ = 7
$R^1$ = 2, 3 or 4
$R^2$ = 11, 12, 13 or 15 substituted at the 4-position
$R^4$ = 8, 9, 10, 11, 12 or 15 substituted at the 6-, 7- or 8-position
$R^3$, $R^5$ = 7
$R^1$ = 2, 3 or 4
$R^2$ = hydroxy, methoxy or acetoxy substituted at the 4-position
$R^4$ = 8, 9, 10, 11, 12 or 15 substituted at the 6-, 7- or 8-position
$R^3$, $R^5$ = 7
$R^1$ = 2, 3 or 4
$R^2$ = 11, 12, 13 or 15 substituted at the 4-position
$R^4$ = fluorine, chlorine, methyl, trifluoromethyl, methoxy, methylthio or hydroxy substituted at the 6-, 7- or 8-position
$R^3$, $R^5$ = 7
$R^1$ = methyl
$R^2$ = 11, 12, 13 or 15 substituted at the 4-position
$R^4$ = 8, 9, 10, 11, 12 or 15 substituted at the 6-, 7- or 8-position
$R^3$, $R^5$ = 7
$R^1$ = methyl
$R^2$ = hydroxy, methoxy or acetoxy substituted at the 4-position
$R^4$ = 8, 9, 10, 11, 12 or 15 substituted at the 6-, 7- or 8-position
$R^3$, $R^5$ = 7
$R^1$ = methyl
$R^2$ = 11, 12, 13 or 15 substituted at the 4-position
$R^4$ = fluorine, chlorine, methyl, trifluoromethyl, methoxy, methylthio or hydroxy substituted at the 6-, 7- or 8-position
$R^3$, $R^5$ = 7
$R^1$ = methyl
$R^2$ = methoxy, hydroxy or acetoxy substituted at the 4-position
$R^4$ = fluorine, chlorine, methyl, trifluoromethyl, methoxy, methylthio or hydroxy substituted at the 6-, 7- or 8-position
$R^3$, $R^5$ = 7
$R^1$ = methyl
$R^2$ = methoxy, hydroxy or acetoxy substituted at the 4-position
$R^4$ = fluorine or chlorine substituted at the 6-, 7- or 8-position Particular compounds of the invention are described in the Examples and of these preferred compounds are those wherein
$R^1$ = methyl
$R^2$ = acetoxy substituted at the 4-position
$R^4$ = chlorine substituted at the 6-position
$R^3$, $R^5$ = hydrogen
A = S
$R^1$ = methyl
$R^2$ = acetoxy substituted at the 4-position
$R^3$, $R^4$, $R^5$ = hydrogen
A = SO A suitable pharmaceutically-acceptable acid-addition salt of the invention is, for example, a hydrochloride, hydrobromide, phosphate or sulphate, or a citrate, acetate, maleate or oxalate.

The thioxanthene derivatives of the invention may be manufactured by methods known in themselves for the manufacture of chemically analogous compounds, $R^1$, $R^2$, $R^3$, $R^4$ and $R^5$ having the meaning stated above, for example:

a. for those compounds in which $R^1$ has a value other than that numbered 1 or 6 and $R^2$, $R^3$, $R^4$ and $R^5$ have values other than those numbered 10, 13 or 15, reaction of a compound of the formula III:

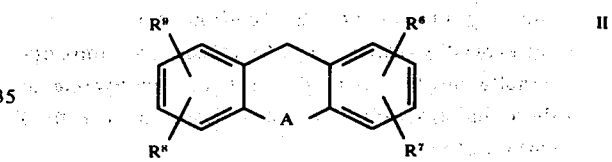

wherein $R^6$, $R^7$, $R^8$ and $R^9$ have the values stated above for $R^2$, $R^3$, $R^4$ and $R^5$ other than those numbered 10, 13 or 15, with a compound of the formula $R^{10}N(CH_2CH_2X)_2$ wherein $R^{10}$ has the value stated above for $R^1$ other than that numbered 1 or 6 and X is a displaceable radical. X may be, for example, a displaceable halogen atom, for example a chlorine or bromine atom, or an arensulphonyloxy or alkanesulphonyloxy radical, for example a toluene-p-sulphonyloxy or methanesulphonyloxy radical. The reaction is preferably conducted in the presence of a base, for example sodium methylsulphinylmethide, in a diluent or solvent, for example dimethyl sulphoxide, and is preferably conducted in an inert atmosphere.

b. for those compounds in which $R^2$, $R^3$, $R^4$ or $R^5$ have values other than those numbered 10 or 13, reaction of a compound of the formula IV:

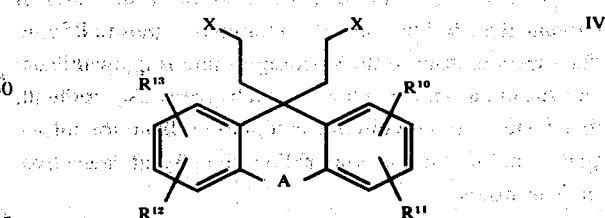

wherein $R^{10}$, $R^{11}$, $R^{12}$ and $R^{13}$ have the values stated above for $R^2$, $R^3$, $R^4$ and $R^5$ other than those numbered 10 or 13 and X has the value stated above, with a compound of the formula $R^1NH_2$. The reaction may be conducted by heating the reactants together, optionally in the presence of a diluent or solvent such as ethanol or xylene. Where a temperature higher than the boiling point of the diluent or solvent is required, the reaction may be conducted in a pressure vessel.

c. for those compounds in which $R^1$ is an alkyl or cycloalkylalkyl radical and $R^2$, $R^3$, $R^4$ and $R^5$ have values other than those numbered 10 or 13, reducing a compound of the formula V:

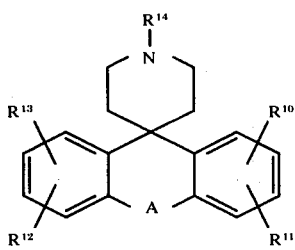

V wherein $R^{10}$, $R^{11}$, $R^{12}$ and $R^{13}$ have the meanings stated above and wherein $R^{14}$ is an alkanoyl or cycloalkanoyl radical. The reduction may be carried out with a complex metal hydride, for example lithium aluminium hydride, in a diluent or solvent such as diethyl ether or tetrahydrofuran. It may be accelerated or completed by the application of heat, for example by heating to the boiling point of the diluent or solvent.

d. for those compounds in which $R^1$ is a hydrogen atom and $R^2$, $R^3$, $R^4$ and $R^5$ have values other than that numbered 13, hydrolysis of a compound of the formula VI:

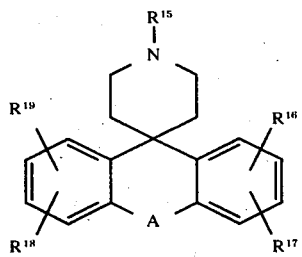

VI wherein $R^{15}$ is an acyl, alkanesulphonyl or arenesulphonyl radical and $R^{16}$, $R^{17}$, $R^{18}$ and $R^{19}$ have the values stated above for $R^2$, $R^3$, $R^4$ and $R^5$ other than that numbered 13. $R^{15}$ may, for example, be an alkanoyl, aroyl, alkoxycarbonyl or aryloxycarbonyl radical. The hydrolysis may be carried out with a base, for example sodium or potassium hydroxide, in a diluent or solvent, for example ethanol or aqueous ethanol, and the hydrolysis may be accelerated or completed by the application of heat, for example by heating to the boiling point of the diluent or solvent.

e. for those compounds in which at least one of $R^2$, $R^3$, $R^4$ and $R^5$ is a hydroxy radical and the remaining members of $R^2$, $R^3$, $R^4$ and $R^5$ have values other than those numbered 11, 12 or 13, replacement by hydrogen of the alkyl part of the alkoxy radical in a compound of the formula VII:

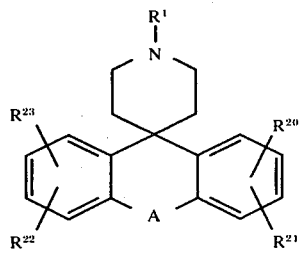

VII wherein at least one of $R^{20}$, $R^{21}$, $R^{22}$ and $R^{23}$ is an alkoxy radical and the remaining members of $R^{20}$, $R^{21}$, $R^{22}$ and $R^{23}$ have the values stated above for $R^2$, $R^3$, $R^4$ and $R^5$ other than those numbered 11, 12 or 13. The reaction may be carried out with an acid, for example HBr in acetic acid at reflux or with aqueous 48% w/v HBr at reflux; with boron tribromide in a solvent such as methylene chloride; with pyridine hydrochloride, for example by heating at 200° C.; with sodium ethanethiolate or sodium thiophenoxide, for example by heating either without additional solvent, or in a solvent such as dimethyl formamide, at 100°–150° C.; or with lithium iodide.

f. for those compounds in which $R^1$ has a value other than that numbered 1 or 10, at least one of $R^2$, $R^3$, $R^4$ and $R^5$ is an alkanoyloxy radical and the remaining members of $R^2$, $R^3$, $R^4$ and $R^5$ have values other than those numbered 14 or 15, reaction of a compound of the formula VIII:

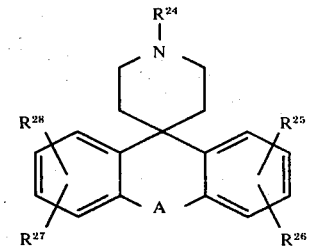

VIII wherein $R^{24}$ has the value stated above for $R^1$ other than that numbered 1 or 10, at least one of $R^{25}$, $R^{26}$, $R^{27}$ and $R^{28}$ is a hydroxy radical and the remaining members of $R^{25}$, $R^{26}$, $R^{27}$ and $R^{28}$ have the values stated above for $R^2$, $R^3$, $R^4$ and $R^5$ other than those numbered 14 or 15, with an alkanoic acid or an acylating agent derived therefrom. The alkanoic acid may, for example, be acetic acid and the derived acylating agent may be the corresponding anhydride or acid chloride. The reaction is preferably carried out in a basic solvent such as pyridine.

g. for those compounds in which $R^1$ is a hydrogen atom and $R^2$, $R^3$, $R^4$ and $R^5$ have values other than those numbered 10 or 13, replacement by hydrogen of the cyano radical in a compound of the formula IX:

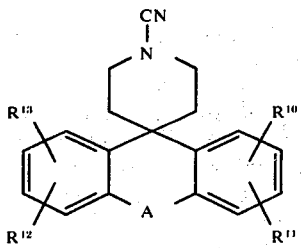

wherein $R^{10}$, $R^{11}$, $R^{12}$ and $R^{13}$ have the meanings stated above. The replacement may be achieved by reaction with a complex metal hydride, for example lithium aluminium hydride, and it may be conducted in a diluent or solvent such as diethyl ether or tetrahydrofuran.

The thioxanthene derivative of the invention may be converted into a pharmaceutically-acceptable acid-addition salt by conventional means.

The starting materials for use in the processes of the invention may be prepared, from known compounds, as described in the Examples. The following summary illustrates the general reactions involved.

The starting material of the formula III for use in process (a) may be prepared by reaction of the appropriate 2-halobenzoic acid with the appropriate thiophenol as described in Examples 12, 17, 23 or 25. The resulting acid is cyclised to the corresponding thioxanthone which is subsequently reduced to the corresponding thioxanthene.

The starting material of the formula IV for use in process (b) may be prepared by dialkylation of the appropriate thioxanthene with 2-chloroethyl vinyl ether as described in Example 2, 17 or 23. The divinyl ether is then hydrolysed and the resulting diol reacted with a reagent which replaces OH with a displaceable radical, for example a halogenating agent or methanesulphonyl chloride.

The starting material of the formula V for use in process (c) may be prepared by reacting the free NH compound with an alkanoyl or cycloalkanoyl halide.

The starting material of the formula VI for use in process (d) may be prepared as for the compound of the formula V. Alternatively an N-alkyl or N-arylalkyl derivative may be reacted with an alkyl or aryl chloroformate, to produce the N-alkoxycarbonyl or N-aryloxycarbonyl derivative respectively.

The starting material of the formula IX for use in process (g) may be prepared by reaction of the corresponding NH compound with cyanogen bromide.

Those starting materials in which A is a sulphinyl or sulphonyl radical may be prepared by oxidation of the corresponding derivative in which A is a sulphur atom, for example with iodobenzene dichloride and hydrogen peroxide respectively.

The preparations of specific starting materials are described inter alia in Examples 2, 5, 6, 7, 9, 10, 11, 12, 13, 17, 20, 21, 22, 23, 25 and 26.

The compounds of the invention have analgesic activity in warm blooded animals. This is demonstrated by activity on a number of standard tests for detecting analgesic activity, for example the mouse writhing test (Collier et al., Brit. J. Pharmac. Chemother., 1968, 32, 295; Whittle, Brit. J. Pharmac. Chemother., 1964, 22, 246) and the mouse tail clip test (Bianchi and Franceschini, Brit. J. Pharmac. Chemother., 1954, 9, 280). These tests are carried out as follows:

Tail Clip test

Ten Female mice of bodyweight approximately 20 g. each are dosed subcutaneously with the compound under test. Twenty minutes later the mice are placed in a plastic arena (30 cm. diameter) and an artery clip is placed on the tail at a distance of 1 cm. from the rump. If an individual mouse does not respond to the painful stimulus of the clip within a 10 second period, it is recorded as analgesed. In this way 50% analgesia corresponds to 5 mice in 10 showing a negative response to the clip.

Writhing test

A painful stimulus is produced by injection of a 0.25% v/v aqueous solution of acetic acid or a 0.03% w/w aqueous solution of acetylcholine into the peritoneum of a female mouse. The characteristic response to this pain is an abdominal contriction in conjunction with a stretching of the body.

Acetic Acid method

Of 12 20 g. female mice, 6 are dosed either subcutaneously or orally with the compound under test and the remaining 6 act as controls. Twenty minutes later all 12 mice receive an injection of the acetic acid solution (0.4 ml.) and are then placed into a plastic container divided into twelve compartments. The number of writhes of each mouse is then recorded over a 15 minute period starting 3 minutes after injection of the agent. The total number of writhes recorded for the treated group is then totalled and compared with the total found for the control group. The results are expressed as % analgesia as follows:

$$100 - \left( \frac{\text{Drug group}}{\text{Control group}} \times 100 \right)$$

Acetylcholine method

Of 12 20 g. female mice, 6 are dosed either subcutaneously or orally with the compound under test and the reamining 6 act as controls. Thirty minutes later all the 12 mice receive an intraperitoneal injection of 0.2 ml. of the acetylcholine solution, and are placed on a plastic platform (30 cm. diameter). Mice which do not writhe during the minute immediately after the injection are said to be analgesed. The results are expressed as % analgesia as follows:

$$\frac{\text{No. of dosed animals not writhing}}{\text{No. of controls writhing}} \times 100$$

(On average approximately 95% of controls respond to the acetylcholine challenge).

All the compounds exemplified in this specification are active on at least one of these standard tests at a dose of equal to or less than 100 mg./kg. of the free base.

The compound of the invention 4-hydroxy-1'-methyl-thioxanthene-9-spiro-4'-piperidine has an oral $LD_{50}$ in mice of greater than 500 mg./kg. The corresponding intravenous $LD_{50}$ is 30 mg./kg. Other $LD_{50}$ values for compounds of the invention when dosed intravenously are as follows:

| $R^1$ | $R^2$ | $R^3$ | $R^4$ | $R^5$ | A | $LD_{50}$ (mg./kg.) |
|---|---|---|---|---|---|---|
| n-Pr | 4-OH | H | H | H | S | 35 |
| Allyl | 4-OH | H | H | H | S | 43 |
| Me | 4-OAc | H | 6-Cl | H | S | >50 |

Within the analgesics of the present invention, at least four sub-classes can be identified:

1. Compounds in which $R^2$, $R^3$, $R^4$ and $R^5$ are other than values 11, 12, 13 or 15 substituted at the 4- or 5-position are neuroleptic analgesics, that is analgesics of the methotrimeprazine type, having a strong sedative component.

2. Compounds in which $R^1$ is a hydrogen atom or a methyl radical, $R^2$ has value 11, 12, 13 or 15 substituted at the 4-position and $R^3$, $R^4$ and $R^5$ are hydrogen atoms are narcotic analgesics, that is analgesics of the morphine type with a range of activities from codeine to morphine.

3. Compounds in which $R^1$ is other than hydrogen or a methyl or ethyl radical, $R^2$ has value 11, 12, 13 or 15 substituted at the 4-position and $R^3$, $R^4$ and $R^5$ are hydrogen atoms are partial agonist analgesics, that is analgesics, of the pentazocine type, which partially antagonise the effect of morphine.

4. Compounds in which $R^1$ is hydrogen or methyl, $R^2$ has value 11, 12, 13 or 15 substituted at the 4-position, $R^4$ has value 8, 9, 10, 11, 12 or 15 substituted at the 6-, 7- or 8-position and $R^3$ and $R^5$ are hydrogen atoms have varying mixtures of analgesic and sedative properties.

According to a further feature of the invention there is provided a pharmaceutical composition which comprises as active ingredient a thioxanthene derivative of the invention in association with a non-toxic pharmaceutically-acceptable diluent or carrier.

The pharmaceutical composition may be, for example, in a form suitable for oral, parenteral or rectal administration, for which purposes it may be formulated by means known to the art into the form of, for example, tablets, capsules, aqueous or oily solutions or suspensions, emulsions, sterile injectable aqueous or oily solutions or suspensions, dispersible powders or suppositories.

The pharmaceutical composition of the invention may also contain, in addition to the thioxanthene derivative, one or more known drugs selected from other analgesic agents, for example, aspirin, paracetamol, phenacetin, codeine, pethidine and morphine, anti-inflammatory agents, for example naproxen, indomethacin and ibuprofen, neuroleptic agents such as chlorpromazine, prochlorperazine, trifluoperazine, and haloperidol and other sedative drugs and tranquillisers such as chlordiazepoxide, phenobarbitone and amylobarbitone.

A preferred pharmaceutical composition of the invention is one suitable for oral administration in unit dosage form, for example tablets and capsules, which contain between 1 and 200 mg. of active ingredient, or one suitable for intravenous, intramuscular or subcutaneous injection, for example a sterile aqueous solution containing between 1 and 50 mg./ml. of active ingredient.

The pharmaceutical composition of the invention will normally be administered to man for the treatment or prevention of pain at such a dose that each patient receives an oral dose of between 30 mg. and 300 mg. of active ingredient, an intramuscular or subcutaneous dose of between 30 and 150 mg. of active ingredient or an intravenous dose of between 15 and 75 mg. of active ingredient, the composition being administered 2 or 3 times per day.

The invention is illustrated, but not limited, by the following Examples in which Example 4 describes the preparation of a starting material.

EXAMPLE 1

A solution of thioxanthene (4.95 g.) in dimethyl sulphoxide (40 ml.) is added rapidly to a solution of sodium methylsulphinylmethide [prepared in the usual way from sodium hydride (4.0 g. of a 60% dispersion in mineral oil) and dimethyl sulphoxide (100 ml.)]. The red coloured mixture is then cooled in an ice bath and a solution of N,N-di-(2-chloroethyl)-N-methylamine hydrochloride (4.8 g.) in dimethylsulphoxide (20 ml.) is added gradually during 15 minutes. The mixture is stirred until the red colour disappears, poured into water (500 ml.), and extracted with ether. To the dried, filtered ethereal solution is added an ethereal solution of citric acid. The precipitate is recrystallised from methanol/ether to give 1'-methylthioxanthene-9-spiro-4'-piperidine citrate, m.p. 188°–190° C. (decomposition).

EXAMPLE 2

A mixture of 9,9-bis(2'-chloroethyl)thioxanthene (2 g.), ethanol (10 ml.) and methylamine (10 ml.; 25% w/v aqueous solution) is heated in a pressure vessel at 150° C. for 17 hours. The solvents are evaporated and the residual gum is shaken with a mixture of ether and sodium bicarbonate solution. The ethereal extract is separated, dried (anhydrous magnesium sulphate) and treated with an ethereal solution of citric acid to give 1'-methylthioxanthene-9-spiro-4'-piperidine citrate, m.p. 190° C. on recrystallisation from ethanol.

The starting material, 9,9-bis-(2'-chloroethyl)-thioxanthene, may be prepared as follows:

A solution of thioxanthene (29.7 g.) in dimethyl sulphoxide (1,200 ml.) is added gradually to a solution of sodium methylsulphinylmethide [prepared in the usual way from sodium hydride (24 g. of a 60% dispersion in mineral oil) and dimethyl sulphoxide (300 ml.)]. The dark red mixture is cooled in ice and chloroethyl vinyl ether (44 g.) is added dropwise. The mixture is stirred under nitrogen for a further 16 hours, allowed to warm to ambient temperature (18°to 20° C.), poured into water (3 l.) and extracted with ether. The ethereal solution is washed with water, dried, and then evaporated to give crude oily 9,9-bis(2'-vinyloxyethyl)thioxanthene.

The unpurified oil, ethanol (300 ml.), water (150 ml.) and concentrated hydrochloric acid (15 ml.) are heated under reflux for 18 hours, cooled and evaporated to a small volume. Water (1,500 ml.) is added and the liquid is decanted from the precipitated gum which is dissolved in ether. The ethereal solution is washed with water (2 × 350 ml.), dried, and the ether evaporated. The residue is crystallised from toluene to give 9,9-bis(2'-hydroxyethyl)thioxanthene, m.p. 132°–135° C.

Thionyl chloride (10 ml.) is added to a suspension of 9,9-bis(2'-hydroxyethyl)thioxanthene (5 g.) in toluene (50 ml.). The solid dissolves with generation of heat and the solution is then gently refluxed for 45 minutes. The solvent and excess thionyl chloride are removed under reduced pressure to give an oil (5.6 g.) which solidifies on cooling. Crystallisation of this solid from ethanol gives 9,9-bis(2'-chloroethyl)thioxanthene, m.p. 61°-62° C.

EXAMPLE 3

The process described in the first part of Example 2 is repeated except that an equivalent amount of the appropriate amine R-NH$_2$ is used in place of methylamine and ethanol is the sole solvent. The following compounds are thus prepared:

| R | Work up base | Salt | m.p. °C. | Recrystallisation solvent |
|---|---|---|---|---|
| Et | NaHCO$_3$ | citrate | 185-186 (decomp.) | ethanol |
| Pr$^i$ | NaHCO$_3$ | hydrogen sulphate | 258-260 (decomp.) | ethanol/ether |
| Pr$^n$ | NaHCO$_3$ | hydrogen sulphate | 245-248 | ethanol/ether |
| H | NaHCO$_3$ | sulphate monohydrate | 314-316 (decomp.) | ethanol/water |
| Bu$^n$ | — | free base | 125-127 | ethanol |
| Amyl | NaOH | free base | 90-92 | ethanol/water |
| Hexyl | NaOH | hydrochloride hydrate | 100-106 | ethanol/ether |
| Allyl | — | hydrogen sulphate | 232-235 (decomp.) | butanol |

EXAMPLE 4

A mixture of 9,9-bis(2'-chloroethyl)thioxanthene (3.4 g.) and benzylamine (10 ml.) is heated under reflux for 2 hours, cooled diluted with water (100 ml.) and acidified with concentrated hydrochloric acid. The liquid is decanted from the residual gum which is triturated with water (200 ml.) when it solidifies. The solid is crystallised from ethanol to give 1'-benzylthioxanthene-9-spiro-4'-piperidine, m.p. 248° C. Addition of ether to the ethanolic filtrate remaining after removal, by filtration, of the base, yields 1'-benzylthioxanthene-9-spiro-4'-piperidine hydrochloride, m.p. 263°-266° C.

EXAMPLE 5

A mixture of 2-chloro-9,9-bis(2'-chloroethyl)-thioxanthene (0.9 g.), aqueous methylamine (10 ml.; 40% w/v.) and ethanol (15 ml.) is heated at 150° C. for 17 hours in a sealed tube. The cooled reaction mixture is diluted with water (50 ml.), basified with sodium bicarbonate solution and extracted with chloroform. The chloroform extract is dried (MgSO$_4$), filtered, and evaporated. The residual gum (0.5 g.) is chromatographed on silica gel using ethanol/ethyl acetate (2:1) eluant. The product obtained after evaporation of the solvent is dissolved in ether, treated with an ethereal solution of oxalic acid, and the precipitated oxalate is dried at 80° C. in vacuo when there is obtained 2-chloro-1'-methylthioxanthene-9-spiro-4'-piperidine oxalate monohydrate (0.45 g.), m.p. 152°-155° C. (decomposition).

The 2-chloro-9,9-bis(2'-chloroethyl)thioxanthene used as starting material may be prepared as follows:

The second, third and fourth parts of Example 2 are repeated using an equivalent amount of 2-chlorothioxanthene as starting material in place of thioxanthene and there are thus obtained 2-chloro-9,9-bis(2'-vinyloxyethyl)thioxanthene, 2-chloro-9,9-bis(2'-hydroxyethyl)thioxanthene, m.p. 129° C. from petroleum ether (b.p. 60°-80° C.)/chloroform and 2-chloro-9,9-bis(2'-chloroethyl)thioxanthene, m.p. 75°-80° C., respectively.

EXAMPLE 6

The first part of Example 2 is repeated using an equivalent amount of 2-methoxy-9,9-bis(2'-chloroethyl)-thioxanthene as starting material in place of 9,9-bis(2'-chloroethyl)thioxanthene, and there is thus obtained 2-methoxy-1'-methylthioxanthene-9-spiro-4'-piperidine, m.p. 106°-107° C. on recrystallisation from aqueous ethanol.

The 2-methoxy-9,9-bis(2'-chloroethyl)thioxanthene used as starting material may be obtained as follows:

The second, third and fourth parts of Example 2 are repeated using an equivalent amount of 2-methoxythioxanthene as starting material in place of thioxanthene and there are thus obtained 2-methoxy-9,9-bis(2'-vinyloxyethyl)-thioxanthene, 2-methoxy-9,9-bis(2'-hydroxyethyl)thioxanthene, m.p. 89°-95° C., and 2-methoxy-9,9-bis(2'-chloroethyl)-thioxanthene, m.p. 106°-108° C. on recrystallisation from ethanol, respectively.

EXAMPLE 7

The first part of Example 2 is repeated using an equivalent amount of 9,9-bis(2'-chloroethyl)thioxanthene 10,10-dioxide as starting material in place of 9,9-bis(2'-chloroethyl)thioxanthene, and there is thus obtained 1'-methylthioxanthene-9-spiro-4'-piperidine 10,10-dioxide hydrochloride, m.p. 296°-297° C. on recrystallisation from ethanol/ether.

The 9,9-bis(2'-chloroethyl)thioxanthene 10,10-dioxide used as starting material may be obtained as follows:

A solution of 9,9-bis(2'-chloroethyl)thioxanthene (3 g.) in glacial acetic acid (60 ml.) is stirred and heated on the steam bath (95°-100° C.) and hydrogen peroxide (3 ml. 30% w/v) is added. 15 Minutes later a further quantity (1.5 ml.) of hydrogen peroxide is added and the mixture is heated for 1 hour longer. The mixture is cooled, diluted with water (200 ml.), and the solid is filtered off and crystallised from petroleum ether (b.p. 100°-120° C.) to give 9,9-bis(2'-chloroethyl)thioxanthene 10,10-dioxide, m.p. 186°-190° C.

EXAMPLE 8

The first part of Example 7 is repeated, using an equivalent amount of the appropriate amine RNH$_2$ in place of methylamine, in ethanol as sole solvent. The following compounds are thus prepared:

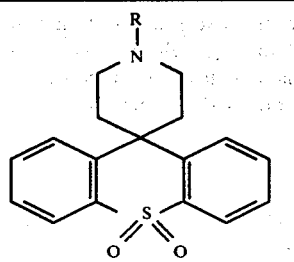

| R | Work up base | m.p. ° C. | Recrystallisation solvent |
|---|---|---|---|
| Et | NaOH | 168–170 | ethanol/water |
| Pr$^i$ | NaOH | 140–142 | ethanol |
| Allyl | NaOH | 150–152 | ethanol/water |

EXAMPLE 9

The first part of Example 7 is repeated except that an equivalent amount of 9,9-bis(2'-chloroethyl)-thioxanthene 10-oxide is used as starting material in place of 9,9-bis(2'-chloroethyl)thioxanthene 10,10-dioxide. There is thus obtained 1'-methylthioxanthene-9-spiro-4' piperidine 10-oxide hydrochloride, m.p. 225°–226° C. on recrystallisation from ethanol/ether.

The 9,9-bis(2'-chloroethyl)thioxanthene 10-oxide used as starting material may be obtained as follows :

A solution of 9,9-bis(2'-chloroethyl)thioxanthene in pyridine (25 ml.) and water (5 ml.) is cooled in an ice/salt bath to —5° to 0° C. and a solution of iodobenzene dichloride (2.7 g.) in dry pyridine (10 ml.) is added slowly during 15 minutes with stirring. Stirring at 0° C. is continued for a further 15 minutes, the reaction mixture is poured into water, acidified with concentrated hydrochloric acid and extracted with chloroform. The product is crystallised from cyclohexane to give 9,9-bis(2'-chloroethyl)-thioxanthene 10-oxide, m.p. 126°–127° C.

EXAMPLE 10

A mixture of 1'-phenoxycarbonylthioxanthene-9-spiro-4'-piperidine (1.6 g.), potassium hydroxide (10 g.), water (20 ml.) and ethanol (20 ml.) is heated under reflux for 30 hours, poured into cold water (100 ml.) and extracted with ether. The ethereal solution is evaporated to give a gum which is dissolved in ethanol and treated with 2N sulphuric acid to give a white precipitate which is recrystallised from 50% aqueous ethanol. There is thus obtained thioxanthene-9-spiro-4'-piperidine sulphate monohydrate, m.p. 314°–316° C. (decomposition).

The 1'-phenoxycarbonylthioxanthene-9-spiro-4'-piperidine used as starting material may be obtained as follows :

To a stirred solution of 1'-benzylthioxanthene-9-spiro-4'-piperidine (2 g.) in methylene chloride (25 ml.) is added dropwise a solution of phenyl chloroformate (0.88 g.) in methylene chloride (15 ml.) at room temperature during 10 minutes. Stirring is continued for 18 hours, the methylene chloride is shaken with 1.0N sodium hydroxide solution, washed with water and dried (Na$_2$SO$_4$). The solution is filtered, the solvent evaporated and the residual oily product is crystallised from ethanol to give 1'-phenoxycarbonyl-thioxanthene-9-spiro-4'-piperidine, m.p. 149°–151° C.

EXAMPLE 11

The first part of Example 2 is repeated except that an equivalent amount of 2-methoxy-9,9-bis(2'-chloroethyl)-thioxanthene 10,10-dioxide is used as starting material in place of 9,9-bis(2'-chloroethyl)thioxanthene. There is thus obtained 2-methoxy-1'-methylthioxanthene-9-spiro-4'-piperidine 10,10-dioxide, m.p. 165°–168° C. on recrystallisation from aqueous ethanol.

The 2-methoxy-9,9-bis(2'-chloroethyl)thioxanthene 10,10-dioxide used as starting material may be obtained as follows:

The second part of Example 7 is repeated except that an equivalent amount of 2-methoxy-9,9-bis(2'-chloroethyl)thioxanthene is used in place of 9,9-bis(2'chloroethyl)thioxanthene. There is thus obtained 2-methoxy-9,9-bis-(2'chloroethyl)thioxanthene 10,10-dioxide, m.p. 159°–160° C. on recrystallization from ethanol.

EXAMPLE 12

To a melt of pyridine hydrochloride (19 g.) at 160° C. is added 4-ethoxy-1'-methylthioxanthene-9-spiro-4'-piperidine (1.3 g.). The stirred mixture is heated to 210° C. for 30 minutes and then cooled, diluted with water and made alkaline with aqueous sodium hydroxide solution. A small amount of solid material is removed by filtration and the filtrate is acidified with concentrated hydrochloric acid followed by neutralisation with sodium bicarbonate and extraction with chloroform. The chloroform extract is evaporated to dryness and the residual yellow gum crystallised from aqueous ethanol to give 4-hydroxy-1'-methylthioxanthene-9-spiro-4'-piperidine, m.p. 180°–182° C.

The starting material, 4-ethoxy-1'-methylthioxanthene-9-spiro-4'-piperidine, may be prepared as follows:

A mixture of 2-ethoxythiophenol (30.8 g.), 2-iodobenzoic acid (49.6 g.), potassium hydroxide pellets (50.0 g.), copper bronze (2.0 g.) and water (500 ml.) is heated under reflux for 20 hours. The mixture is filtered hot and the filtrate is cooled and acidified with concentrated HCl. The fawn precipitate is collected and recrystallised from ethanol to give 2'-ethoxydiphenylsulphide-2-carboxylic acid, m.p. 168° C.

A solution of 2'-ethoxydiphenylsulphide-2-carboxylic acid (20 g.) in trifluoroacetic anhydride (120 ml.) is heated under reflux for 18 hours and the solvent then removed by evaporation in vacuo. The residue is slurried with water, the mixture made alkaline with concentrated sodium hydroxide solution and the suspended solid filtered, dried and recrystallised from ethanol to give 4-ethoxythioxanth-9-one, m.p. 112°–115° C.

A solution of 4-ethoxythioxanth-9-one (4.4 g.) in n-butanol (100 ml.) is heated under reflux and sodium (6.0 g.) is added in portions to the boiling solution. Heating is continued until all the sodium has reacted, and the solvent is then removed by evaporation in vacuo. The residue is slurried with water, extracted with ether (3 × 50 ml.), the extracts dried and evaporated to give 4-ethoxythioxanthene, m.p. 95°–98° C. on recrystallisation from ethanol.

The process described in Example 2 is repeated except that an equivalent amount of 4-ethoxythioxanthene is used in place of thioxanthene. There are thus obtained 4-ethoxy-9,9-bis(2'-hydroxyethyl)thioxanthene, m.p. 143°–145° C. from toluene, 4-ethoxy-9,9- bis-(2'-chloroethyl)thioxanthene, m.p. 134°–136° C., and 4-ethoxy-1'-methylthioxanthene-9-spiro-4'-piperidine, m.p. 139°–142° C., respectively.

Alternatively the process described in Example 1 is repeated except that an equivalent amount of 4-ethoxythioxanthene is used in place of thioxanthene, and there is thus obtained 4-ethoxy-1'-methylthioxanthene-9-spiro-4'-piperidine, m.p. 139°–142° C.

EXAMPLE 13

The process described in the first part of Example 2 is repeated except that equivalent amounts of allylamine and 4-methoxy-9,9-bis(2'-chloroethyl)thioxanthene are used in place of methylamine, and 9,9-bis(2'-chloroethyl)thioxanthene respectively and ethanol is the sole solvent. There is thus obtained 4-methoxy-1'-allylthioxanthene-9-spiro-4'-piperidine m.p. 110°–111° C. after recrystallization from isopropanol.

The starting material 4-methoxy-9,9-bis(2'-chloroethyl)thioxanthene may be prepared as follows:

The second, third, fourth and fifth parts of Example 12 are repeated using an equivalent amount of 2-methoxythiophenol as starting material in place of 2-ethoxythiophenol. There are thus obtained 2'-methoxydiphenylsulphide-2-carboxylic acid, m.p. 193° C. from ethanol, 4-methoxythioxanth-9-one m.p. 166°–168° C. from ethanol, 4-methoxythioxanthene m.p. 81°–82° C. from ethanol, 4-methoxy-9,9-bis(2'-vinyloxyethyl)thioxanthene, 4-methoxy-9,9-bis(2'-hydroxyethyl)thioxanthene, m.p. 148°–149° C. from toluene, and 4-methoxy-9,9-bis(2'-chloroethyl)thioxanthene, m.p. 104°–106° C. from cyclohexane, respectively.

EXAMPLE 14

The process described in Example 13 is repeated except that an equivalent amount of the appropriate amine R—NH$_2$ is used in place of allylamine. The following compounds are thus prepared:

| R | Work up base | Salt | m.p. ° C. | Recrystallisation solvent |
|---|---|---|---|---|
| Pr$^n$ | NaOH | Free base | 129–130 | isopropanol |
| CH$_3$\\>=CH—CH$_3$ / CH$_3$ | NaOH | Hydrochloride | 242–245 (decomp.) | chloroform/ethyl acetate |
| ▷—CH$_2$ | NaOH | Hydrochloride hemihydrate | 212–216 (decomp.) | ethanol ethyl acetate |

EXAMPLE 15

A solution of ethanethiol (1.49 ml.) in dry dimethylformamide (30 ml.) in an atmosphere of nitrogen is treated portionwise with sodium hydride (800 mg. of a 60% dispersion in mineral oil), with stirring at 20°–25° C. After 15 mins. the internal temperature is raised to 100° C. and the 4-methoxy-1'-allylthioxanthene-9-spiro-4'-piperidine (1.685 g.) is added in one portion. The solution is heated at 100° C. for 45 mins., cooled to ambient temperature, poured into water (300 ml.), acidified with concentrated HCl, the mixture filtered and the filtrate rebasified with solid sodium carbonate and extracted three times with ethyl acetate. The combined ethyl acetate extracts are washed with water, dried over MgSO$_4$ and then evaporated, to give 4-hydroxy-1'-allylthioxanthene-9-spiro-4'-piperidine m.p. 224° C. on recrystallisation from methanol/dimethylformamide/water.

EXAMPLE 16

The process described in Example 15 is repeated except that an equivalent amount of the appropriate 1'-substituted-4-methoxythioxanthene-9-spiro-4'-piperidine is used as starting material in place of 1'-allyl-4-methoxythioxanthene-9-spiro-4'-piperidine. The following compounds are thus prepared:

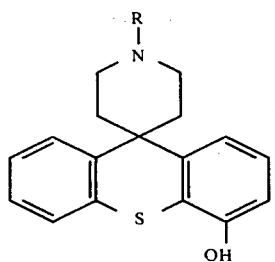

| R | Salt | m.p. °C. | Recrystallisation solvent |
|---|---|---|---|
| CH₃\C=CH—CH₂ / CH₃ | Free base hemihydrate | 120° C. | Water/isopropanol |
| Pr<sup>n</sup> | Free base | 229–230° C. | Water/dimethylformamide/ethanol |
| ▷—CH₂ | Hydrochloride | dec. >270° C. | Methanol/ether |

Note:
When the starting material is the free base, 4 eq. of NaSEt used.
When the starting material is the salt, 5 eq. of NaSEt used.

EXAMPLE 17

The process described in Example 2 is repeated using an equivalent amount of 4,5-dimethoxy-9,9-bis(2'-methanesulphonyloxyethyl)thioxanthene in place of 9,9-bis(2'-chloroethyl)thioxanthene as starting material. There is thus obtained 4,5-dimethoxy-1'-methylthioxanthene-9-spiro-4'-piperidine, m.p. 212°–214° C. from ethanol.

The starting material, 4,5-dimethoxy-9,9-bis-(2'-methanesulphonyloxyethyl)thioxanthene may be prepared as follows:

A mixture of 2-methoxythiophenol (35.0 g.), 2-chloro-3-methoxybenzoic acid (23.4 g.), anhydrous K₂CO₃ (34.5 g.), cuprous iodide (1.25 g.), copper bronze (1.25 g.) and nitrobenzene (312 ml.) is heated at 130° C. (internal temperature) for 3 hours. The mixture is cooled and the product precipitated as its potassium salt with sodium dried ether (2 l.). The brown solid is collected, washed with dry ether, dissolved in water (500 ml.), filtered through diatomaceous earth, acidified with concentrated HCl and extracted three times with ether. The combined ether extracts are washed with water, dried over MgSO₄, treated with carbon, filtered through diatomaceous earth and the ether solution evaporated to dryness. The solid residue is recrystallised from toluene to give 2,2'-dimethoxydiphenylsulphide-6-carboxylic acid m.p. 160°–161° C.

A stirred mixture of 2,2'-dimethoxydiphenylsulphide-2-carboxylic acid (18.7 g.) and polyphosphoric acid (93 g.) is heated on the steam bath for 15 minutes. The hot red solution is added, with stirring, to a mixture of concentrated ammonium hydroxide solution (124 ml.) and ice-water (186 ml.). The yellow solid is filtered, washed with water, dried and recrystallised from ethanol/dimethylformamide to give 4,5-dimethoxythioxanth-9-one m.p. 248°–250° C. The fourth part of Example 12 is repeated except that an equivalent amount of 4,5-dimethoxythioxanth-9-one replaces 4-ethoxythioxanth-9-one and n-propanol is the sole solvent. There is thus obtained after recrystallisation from isopropanol 4,5-dimethoxythioxanthene m.p. 148°–150° C.

The second and third parts of Example 2 are repeated using an equivalent amount of 4,5-dimethoxythioxanthene as starting material in place of thioxanthene and there are thus obtained 4,5-dimethoxy-9,9-bis(2'-vinyloxyethyl)thioxanthene, m.p. 100°–102° C. from isopropanol, and 4,5-dimethoxy-9,9-bis-(2'-hydroxyethyl)thioxanthene m.p. 180°–181° C. from ethanol, respectively.

Methanesulphonyl chloride (1.71 ml.) is added dropwise over 5 minutes at 5° C. to a solution of 4,5-dimethoxy-9,9-bis(2'-hydroxyethyl)thioxanthene (3.46 g.), and triethylamine (4.18 ml.) in dry methylene chloride (70 ml.) with stirring. The mixture is stirred for 15 minutes, diluted with methylene chloride (70 ml.) and washed successively with water, 10% aqueous HCl, a saturated solution of NaHCO₃ and brine. The solution is dried over MgSO₄ and evaporated to dryness. The solid residue is recrystallised from ethanol to give 4,5-dimethoxy-9,9-bis(2'-methanesulphonyloxyethyl)thioxanthene, m.p. 176°–178° C.

EXAMPLE 18

The process described in Example 15 is repeated except that an equivalent amount of 4,5-dimethyoxy-1'-methylthioxanthene-9-spiro-4'-piperidine is used as starting material in place of 4-methoxy-1'-allylthioxanthene-9-spiro-4'-piperidine. There is thus obtained 4,5-dihydroxy-1'-methylthioxanthene-9-spiro-4'-piperidine maleate hemihydrate m.p. >300° C. on recrystallisation from methanol/ether.

EXAMPLE 19

A suspension of 4,5-dihydroxy-1'-methylthioxanthene-9-spiro-4'-piperidine (500 mg.), acetic anhydride (0.32 ml.) and dry pyridine (5 ml.) is stirred at ambient temperature for 24 hours. The solvent is evaporated and the residue is recrystallised from isopropanol to give 4,5-diacetoxy-1'-methylthioxanthene-9-spiro-4'-piperidine acetate, m.p. 121°–126° C. on recrystallisation from isopropanol.

EXAMPLE 20

The process described in the first part of Example 13 is repeated using equivalent amounts of amine RNH₂ and 4-methoxy-9,9-bis(2'-methanesulphonyloxyethyl)-thioxanthene in place of allylamine and 4-methoxy-9,9-bis(2'-chloroethyl)thioxanthene respectively. The following compounds are thus prepared:

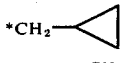

| R | Molar Ratio RNH₂/Dimesylate | Salt | m.p. (° C.) | Recrystallisation solvent |
|---|---|---|---|---|
| CH₂—CH=CH₂ | 5 | HCl . H₂O | 241–242 | ethanol/ethyl acetate |
| CH₂CH₂CH₃ | 5 | HCl . H₂O | 203–205 | ethanol/ether |
| *CH₂—△ | 3 | HCl . H₂O | 215 (decomp.) | methanol/ether |
| CH₂—C(CH₃)=CH₂ | 3.0 | HCl | 249–251 (decomp.) | ethanol/ether |

*The reaction is carried out with cyclopropylmethylamine hydrochloride and 1.25 molar equivalent of anhydrous sodium carbonate.

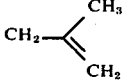

| R | Salt | m.p. (° C.) | Recrystallisation solvent |
|---|---|---|---|
| CH₂CH₃ | HCl | 215 | ethanol/ethyl acetate/ether |
| CH₂CH₂OH | HCl | 227–229 | ethyl acetate |
| CH₃ | HCl . H₂O | 165–167 | ethyl acetate/ethanol/ether |

The starting material, 4-methoxy-9,9-bis(2'-methanesulphonyloxyethyl)thioxanthene, may be prepared as follows:

The fifth part of Example 17 is repeated using an equivlent amount of 4-methoxy-9,9-bis(2'-hydroxyethyl)thioxanthene as starting material in place of 4,5-dimethoxy-9,9-bis(2'-hydroxyethyl)thioxanthene. There is thus obtained 4-methoxy-9,9-bis(2'-methanesulphonyloxyethyl)thioxanthene, m.p. 122°–123° C. on recrystallisation from methanol.

EXAMPLE 21

The process described in the first part of Example 2 is repeated using amine RNH₂ and 4-methoxy-9,9-bis(2'-methanesulphonyloxyethyl)thioxanthene-10,10-dioxide in place of methylamine and 9,9-bis(2'-chloroethyl)thioxanthene respectively and ethanol as the sole solvent. The reaction is worked up using sodium hydroxide. The following compounds are thus prepared:

The starting material 4-methoxy-9,9-bis(2'-methanesulphonyloxyethyl)thioxanthene-10,10-dioxide may be prepared as follows:

85% w/w Metachloroperbenzoic acid (2.13 g.) is added portionwise to a stirred solution of 4-methoxy-9,9-bis(2'-methanesulphonyloxyethyl)thioxanthene (2.36 g.) in chloroform (24 ml.) at 5°–10° C. The mixture is stirred at 5°–10° C. for 30 minutes and then at ambient temperature overnight. The suspension obtained is washed successively with saturated NaHCO₃ solution and water, dried over MgSO₄ and evaporated to dryness in vacuo. The residual gum on trituration with a small volume of ice-cold absolute ethanol gives 4-methoxy-9,9-bis(2'-methanesulphonyloxyethyl)thioxanthene-10,10-dioxide, m.p. 200°–202° C. on recrystallisation from methanol.

EXAMPLE 22

The process described in the first part of Example 2 is repeated using amine RNH₂ and replacing 9,9-bis(2'-chloroethyl)thioxanthene by 4-methoxy-9,9-bis(2'-methanesulphonyloxyethyl)thioxanthene-10-oxide. Ethanol is the sole solvent and the reaction is worked up with sodium hydroxide. The following compounds are thus prepared:

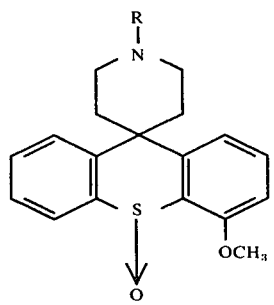

| R | Molar Ratio | RNH₂ Dimesylate | Salt | m.p.(° C.) | Recrystallisation solvent |
|---|---|---|---|---|---|
| CH₂—CH=CH₂ | 3 | | Free base | 167 | ethyl acetate/ petroleum ether (b.p.60–80° C.) |
| CH₃ | * | | HCl . H₂O | 242 | isopropanol/ ether |
| CH₂CH₂CH₃ | 3 | | HCl . H₂O | 215–218 | ethanol/ethyl acetate/ether |

*The reaction is carried out with 22% w/v ethanolic methylamine solution.

The starting material 4-methoxy-9,9-bis(2'-methanesulphonyloxyethyl)thioxanthene-10-oxide may be prepared as follows:

The second part of Example 9 is repeated using an equivalent amount of 4-methoxy-9,9-bis(2'-methanesulphonyloxyethyl)thioxanthene as starting material in place of 9,9-bis(2'-chloroethyl)thioxanthene. There is thus obtained 4-methoxy-9,9-bis(2'-methanesulphonylethyl)thioxanthene-10-oxide, m.p. 169°–170° C. on recrystallisation from methanol.

EXAMPLE 23

The process described in Example 16 is repeated using an equivalent amount of the appropriate 1'-substituted-4-methoxythioxanthene-9-spiro-4'-piperidine derivative as starting material. The following compounds are thus prepared:

| R | R² | A | Reaction Time | Salt | m.p.(° C.) | Recrystallisation solvent |
|---|---|---|---|---|---|---|
| CH₂CH₂OH | H | S | 2 hrs | HCl . H₂O | 173 | ethanol/ethyl acetate/ether |
| CH₃ | H | S | 1½ hrs | Free base | 229–232 | dimethyl formamide/methanol/water |
| CH₂CH=CH₂ | H | SO | 30 mins | HCl . 1-H₂O | 257–260 | ethanol/ether |
| CH₃ | H | SO | 1 hr | HCl . 1½-H₂O | 212 | ethanol/ethyl acetate/ether |
| CH₂CH₂CH₃ | H | SO | 2 hrs | HCl . H₂O | 192–194 | ethanol/ethyl acetate/ether |
| CH₂—CH=CH₂ | H | SO₂ | 15 mins | HCl | 280(decomp.) | methanol |
| CH₂CH₂CH₃ | H | SO₂ | 15 mins | HCl | 287 (decomp.) | methanol/ether |
| CH₂—◁ | H | SO₂ | 15 mins | HCl | 270(decomp.) | methanol/ether |
| CH₃ | Cl | S | 2 hrs | Free base | 257–260 (decomp.) | |

*Purified by slurrying with dimethyl formamide at 100° C.

The starting material, 2-chloro-5-methoxy-1'-methylthioxanthene-9-spiro-4'-piperidine may be prepared as follows:

The second and third parts of Example 17 are repeated using an equivalent amount of 2,5-dichlorobenzoic acid as starting material in place of 2-chloro-3-methoxybenzoic acid and there are thus obtained 2'-methoxy-4-chloro-diphenylsulphide-2-carboxylic acid, m.p. 216° C. on recrystallisation from toluene and 2-chloro-5-methoxythioxanth-9-one, m.p. 191°–193° C. on recrystallisation from ethanol.

An intimate mixture of 2-chloro-5-methoxythioxanth-9-one (8 g.) and aluminium isopropoxide (32 g.)

is heated and stirred in an atmosphere of nitrogen for 3½ hours at 190° C. The mixture is cooled, 2N-hydrochloric acid (210 ml.) is added and the mixture extracted three times with ether. The combined ether extracts are washed with brine, dried over $MgSO_4$ and the solvent evaporated in vacuo to give 2-chloro-5-methoxythioxanthene, m.p. 95°–96° C. on recrystallisation from methanol.

The second and third parts of Example 2 are repeated using an equivalent amount of 2-chloro-5-methoxythioxanthene as starting material in place of thioxanthene and there are thus obtained 2-chloro-5-methoxy-9,9-bis(2'-vinyloxyethyl)thioxanthene (gum used without purification) and 2-chloro-5-methoxy-9,9-bis(2'-hydroxyethyl)thioxanthene, m.p. 175°–178° C. on recrystallisation from ethyl acetate, respectively.

The fifth part of Example 17 is repeated using an equivalent amount of 2-chloro-5-methoxy-9,9-bis(2'-hydroxyethyl)thioxanthene as starting material in place of 4,5-dimethoxy-9,9-bis(2'-hydroxyethyl)thioxanthene and there is thus obtained 2-chloro-5-methoxy-9,9-bis(2'-methanesulphonyloxyethyl)thioxanthene which is obtained as an oil and used without further purification.

The first part of Example 2 is repeated using an equivalent amount of 2-chloro-5-methoxy-9,9-bis(2'-methanesulphonyloxyethyl)thioxanthene as starting material in place of 9,9-bis(2'-chloroethyl)thioxanthene and there is thus obtained 2-chloro-5-methoxy-1'-methylthioxanthene-9-spiro-4'-piperidine as a gum which is used without further purification.

EXAMPLE 24

A solution of 1'-ethyl-4-methoxythioxanthene-9-spiro-4'-piperidine (1.625 g.) in glacial acetic acid (20 ml.) is added to 48% w/v hydrobromic acid (20 ml.) and refluxed with stirring for 5 hours. The mixture is cooled, diluted with water (500 ml.), cooled in ice and basified with 19N-sodium hydroxide solution and the solution washed with ether (× 3). The aqueous alkaline layer is acidfied to pH 1 with concentrated hydrochloric acid, neutralised with solid sodium bicarbonate and extracted with ethyl acetate (× 3). The combined ethyl acetate extracts are washed with water (× 3), dried over $MgSO_4$ and the ethyl acetate removed by distillation in vacuo. The resulting sticky solid is triturated with ether to give 1'-ethyl-4-hydroxythioxanthene-9-spiro-4'-piperidine, m.p. 223°–225° C. on recrystallisation from dimethyl formamide/methanol/water.

EXAMPLE 25

A mixture of 3-chloro-5-methoxy-1'-methylthioxanthene-9-spiro-4'-piperidine hydrochloride monohydrate (1.5 g.) and 48% w/v aqueous hydrobromic acid (30 ml.) is heated under reflux with stirring for 5 hours. The reaction mixture is worked up as described in Example 24 and the product converted to its hydrochloride and recrystallised from ethanol-ether. There is thus obtained 3-chloro-5-hydroxy-1'-methylthioxanthene-9-spiro-4'-piperidine hydrochloride hemihydrate, m.p. 221°–225° C.

The starting material 3-chloro-5-methoxy-1'-methylthioxanthene-9-spiro-4'-piperidine may be prepared as follows:

The second and third parts of Example 17 are repeated using an equivalent amount of 2,4-dichlorobenzoic acid as starting material in place of 2-chloro-3-methoxybenzoic acid and o-dichlorobenzene as solvent and there are thus obtained 2'-methoxy-5-chlorodiphenylsulphide-2-carboxylic acid, m.p. 214°–215° C. on recrystallisation from methanol and 3-chloro-5-methoxythioxanth-9-one, m.p. 223°–225° C. on recrystallisation from dimethyl formamide and methanol, respectively.

A stirred suspension of 3-chloro-5-methoxythioxanth-9-one (13.8 g.) in dry tetrahydrofuran (140 ml.) is treated dropwise with a solution of diborane in tetrahydrofuran (1M, 40 ml.) at ambient temperature and in an atmosphere of argon. The mixture is heated at reflux for 1.25 hours, cooled, diluted carefully with water and extracted with ether (× 3). The combined ether extracts are washed with brine, dried over $MgSO_4$ and then evaporated, to give 3-chloro-5-methoxythioxanthene, m.p. 72°–74° C. on recrystallisation from methanol.

The second and third parts of Example 2 are repeated using an equivalent amount of 3-chloro-5-methoxythioxanthene as starting material in place of thioxanthene and there are thus obtained 3-chloro-5-methoxy-9,9-bis(2'-vinyloxyethyl)thioxanthene (gum used without purification) and 3-chloro-5-methoxy-9,9-bis(2'-hydroxyethyl)thioxanthene, m.p. 198°–199° C. on recrystallisation from isopropanol.

The fifth part of Example 17 is repeated using an equivalent amount of 3-chloro-5-methoxy-9,9-bis(2'-hydroxyethyl)thioxanthene as starting material in place of 4,5-dimethoxy-9,9-bis(2'-hydroxyethyl)thioxanthene and there is thus obtained 3-chloro-5-methoxy-9,9-bis(2'-methanesulphonyloxyethyl)thioxanthene, m.p. 148°–149° C. on recrystallisation from toluene.

The first part of Example 2 is repeated using an equivalent amount of 3-chloro-5-methoxy-9,9-bis(2'-methanesulphonyloxyethyl)thioxanthene as starting material in place of 9,9-bis(2'-chloroethyl)thioxanthene and there is thus obtained 3-chloro-5-methoxy-1'-methylthioxanthene-9-spiro-4'-piperidine hydrochloride monohydrate, m.p. 185°–195° C. on recrystallisation from ethanol/ether.

EXAMPLE 26

A stirred solution of 1'-cyclobutylmethyl-4-methoxythioxanthene-9-spiro-4'-piperidine hydrochloride (600 mg.) in dry methylene chloride (12 ml.) in an atmosphere of nitrogen, protected from light using aluminium foil and at −10° C. (carbontetrachloride/dry-ice bath), is treated with boron tribromide (0.6 ml.) in one portion. The reaction temperature is allowed to rise to ambient temperature and stirring is continued for 1.5 hours. The suspension is cooled in ice, treated dropwise with 2N—NaOH solution until solution is complete. The methylene chloride is distilled off in vacuo and the solution neutralised with glacial acetic acid. The pink solid is filtered off, washed with water and dried in vacuo over phosphorous pentoxide at 60° C. The solid is suspended in hot ethanol, and treated with ethereal hydrochloric acid, causing the solid to dissolve. The hydrochloride crystallises almost immediately to give 1'-cyclobutylmethyl-4-hydroxythioxanthene-9-spiro-4'-piperidine hydrochloride hemihydrate, m.p. 270° C. (decomposition).

The starting material 1'-cyclobutylmethyl-4-methoxythioxanthene-9-spiro-4'-piperidine hydrochloride, may be prepared as follows:

A solution of 1'-benzyl-4-methoxythioxanthene-9-spiro-4'-piperidine (15.48 g.) and cyanogen bromide (4.68 g.) in methylene chloride (155 ml.) is stirred at ambient temperature overnight. The solvent is evaporated in vacuo, the residual gum dissolved in toluene and subjected to chromatography on magnesium silicate (200 g.), eluting consecutively with petroleum ether (b.p. 60°–80° C.) (5 × 200 ml.), toluene (5 × 200 ml.) and chloroform (5 × 200 ml.). The combined chloroform fractions are evaporated in vacuo and the residual gum is triturated with ice-cold ether to give 1'-cyano-4-methoxythioxanthene-9-spiro-4'-piperidine, m.p. 145°–146° C. on recrystallisation from toluene/ether 1/2.5.

A solution of 1'-cyano-4-methoxythioxanthene-9-spiro-4'-piperidine (9 g.) in dry tetrahydrofuran (100 ml.) is added dropwise to a suspension of lithium aluminium hydride (2.12 g.) in tetrahydrofuran (100 ml.) with stirring at 20°–25° C. (cooling is required). The suspension is stirred at ambient temperature for 2 hours and is then treated dropwise with water (2.12 ml.), 2N-sodium hydroxide solution (2.12 ml.) and water (6.36 ml.) consecutively. The suspension is filtered through diatomaceous earth and the residue is washed thoroughly with warm tetrahydrofuran (3 × 100 ml.). The tetrahydrofuran solution is evaporated to dryness in vacuo, the residue is dissolved in toluene (100 ml.) and washed well with water (3 × 25 ml.). The toluene solution is dried over MgSO$_4$ and the solvent is evaporated in vacuo. The residual gum is dissolved in ethyl acetate (50 ml.) and treated with ethereal hydrochloric acid to give 4-methoxythioxanthene-9-spiro-4'-piperidine hydrochloride, m.p. softens at 170° C. and melts at 190° C.

A solution of 4-methoxythioxanthene-9-spiro-4'-piperidine hydrochloride (2.0 g.) in ethanol (5 ml.) is treated with 2N—NaOH solution (5 ml.), diluted with water (50 ml.) and extracted with ether (3 × 50 ml.). The combined ether extracts are washed with brine, dried over MgSO$_4$ and the solvent evaporated in vacuo to give 4-methoxythioxanthene-9-spiro-4'-piperidine (1.5 g.).

Cyclobutanecarboxylic acid chloride (0.77 g.) is added to a solution of the residual gum (1.5 g.) in dry methylene chloride (20 ml.) and triethylamine (0.9 ml.) at 5° C. with stirring. The solution is stirred at ambient temperature overnight, diluted with methylene chloride (80 ml.) and washed successively with water (25 ml.), N—HCl solution (25 ml.), saturated Na$_2$CO$_3$ solution (2 × 25 ml.) and water (25 ml.). The solution is dried over MgSO$_4$, treated with carbon, filtered through diatomaceous earth and the solvent evaporated in vacuo. The residual gum (1.9 g.) is dissolved in the minimum of toluene and subjected to column chromatography on magnesium silicate (190 g.), eluting consecutively with toluene (5 × 200 ml.), 5% v/v ethyl acetate/toluene (12 × 200 ml.), 7½% v/v ethyl acetate/toluene (5 × 200 ml.) and 10% v/v ethyl acetate/toluene. The last eight fractions of 5% v/v ethyl acetate/toluene are combined with the 7½% v/v ethyl acetate/toluene fractions and evaporated to dryness in vacuo to give 1'-cyclobutylcarbonyl-4-methoxythioxanthene-9-spiro-4'-piperidine which is used without further purification.

A solution of the crude 1'-cyclobutylcarbonyl-4-methoxythioxanthene-9-spiro-4'-piperidine (1.4 g.) in dry tetrahydrofuran (14 ml.) is added dropwise to a suspension of lithium aluminium hydride (140 mg.) in dry tetrahydrofuran (10 ml.) with stirring in an atmosphere of nitrogen. The mixture is heated at reflux for 5 minutes, cooled in ice and treated successively with water (0.14 ml.), 2N—NaOH solution (0.14 ml.) and water (0.42 ml.). The suspension is filtered through diatomaceous earth and the residue is washed well with hot tetrahydrofuran. The tetrahydrofuran solution is dried over anhydrous K$_2$CO$_3$ and the solvent evaporated in vacuo. The residual gum is dissolved in methylene chloride (20 ml.) and filtered through basic alumina (Activity III) (30 g.), washing through thoroughly with methylene chloride. The combined solvents are evaporated and the residual gum is dissolved in ether and treated with ethereal hydrochloric acid to give 1'-cyclobutylmethyl-4-methoxythioxanthene-9-spiro-4'-piperidine hydrochloride, m.p. 253°–254° C. on recrystallisation from isopropanol/ether.

EXAMPLE 27

The process described in Example 19 is repeated using the appropriate 1'-substituted-4-hydroxythioxanthene-9-spiro-4'-piperidine derivative as starting material in place of 4,5-dihydroxy-1'-methylthioxanthene-9-spiro-4'-piperidine. The following compounds are thus prepared:

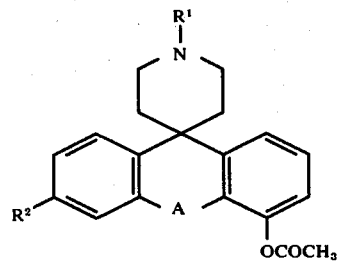

| R$^1$ | R$^2$ | A | Salt | m.p.(° C.) | Recrystallisation solvent |
|---|---|---|---|---|---|
| *CH$_3$ | H | S | HCl . H$_2$O | 96 | ethanol/ethyl acetate/ether |
| CH$_2$—CH=CH$_2$ | H | S | acetate | 95 | ethyl acetate/80–100° C. petrol |
| CH$_3$ | Cl | S | HCl . H$_2$O | 179–181 (decomp.) | ethanol/ether |
| CH$_2$—CH=CH$_2$ | H | SO$_2$ | HCl . 1½-H$_2$O | 180(decomp.) | ethanol/ether |
| CH$_2$-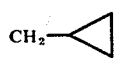 | H | SO$_2$ | HCl . 1½-H$_2$O | 215(decomp.) | ethanol |

-continued

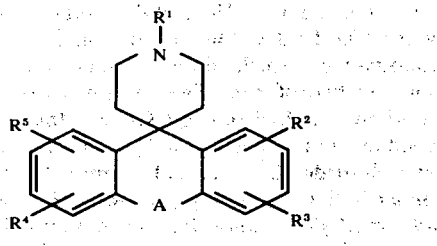

| R¹ | R² | A | Salt | m.p.(° C.) | Recrystallisation solvent |
|---|---|---|---|---|---|
| CH₃ | H | SO | HCl · 2½-H₂O | 189–190 | ethanol/ethyl acetate/ether |

⁽¹⁾In each case where acetic anhydride is the acylating agent, 1.1 equivalents are used.
*Product softens rather than melts, probably because it is very hygroscopic. Mass Spec. m/e 339.

What we claim is:

1. A method of relieving or preventing pain in warm blooded animals including man which comprises administering an analgesically-effective amount of a compound of the formula:

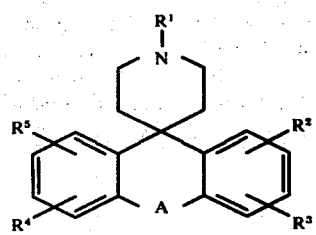

wherein $R^1$ is selected from the group consisting of
1. hydrogen;
2. alkyl of 1 to 10 carbons;
3. alkenyl of 3 to 10 carbons wherein the double bond it contains is separated from the nitrogen atom of the spiropiperidine ring by at least 1 carbon;
4. cycloalkylalkyl of 4 to 7 carbons optionally substituted in the cycloalkyl nucleus by an aryl of 6 to 10 carbons or by one or two alkyls of 1 to 3 carbons;
5. aroylalkyl of 8 to 12 carbons optionally substituted in the aryl nucleus by one to three halogens or alkyls of 1 to 3 carbons; and
6. hydroxyalkyl of 2 to 5 carbons wherein the oxygen atom it contains is separated from the nitrogen atom of the spiropiperidine ring by at least two carbon atoms;

$R^2$, $R^3$, $R^4$ and $R^5$, which may be the same or different, are selected from the group consisting of
7. hydrogen;
8. halogen;
9. alkyl of 1 to 5 carbons;
10. haloalkyl of 1 to 5 carbons;
11. alkoxy of 1 to 5 carbons;
12. alkylthio of 1 to 5 carbons;
13. alkanoyloxy of 1 to 5 carbons;
14. hydroxyalkyl of 1 to 5 carbons; and
15. hydroxy;

A stands for sulphur, sulphinyl or sulphonyl; and the pharmaceutically-acceptable acid-addition salts thereof.

2. The method of claim 1 wherein A stands for sulphur or sulphinyl.

3. The method of claim 1 wherein $R^1$ stands for value 1 or 2, $R^2$ stands for value 11, 12, 13 or 15 substituted at the 4-position and $R^3$, $R^4$ and $R^5$ stand for hydrogens.

4. The method of claim 1 wherein $R^2$ stands for values 8, 9, 10, 11, 12 or 14 substituted at the 2- or 3-position and $R^3$, $R^4$ and $R^5$ stand for hydrogens.

5. The method of claim 1 wherein $R^2$ stands for value 11, 12, 13 or 15 substituted at the 4-position, $R^4$ stands for value 8, 9, 10, 11, 12 or 15 substituted at the 6-, 7- or 8-position and $R^3$ and $R^5$ both stand for hydrogens.

6. The method of claim 1 wherein $R^1$ stands for methyl, $R^2$ stands for methoxy, hydroxy or acetoxy substituted at the 4-position, $R^4$ stands for fluorine, chlorine, methyl, trifluoromethyl, methoxy, methylthio or hydroxy substituted at the 6-, 7- or 8-position and $R^3$ and $R^5$ stand for hydrogens.

7. The method of claim 1 wherein $R^1$ is methyl, $R^2$ is acetoxy substituted at the 4-position, $R^4$ is chlorine substituted at the 6-position, $R^3$ and $R^5$ are hydrogens and A is sulphur.

8. The method of claim 1 wherein $R^1$ is methyl, $R^2$ is acetoxy substituted at the 4-position, $R^3$, $R^4$ and $R^5$ are hydrogens and A is sulphinyl.

9. A thioxanthene derivative of the formula:

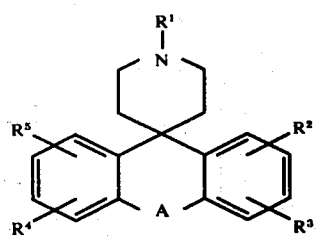

wherein $R^1$ is methyl, $R^2$ is acetoxy substituted at the 4-position, $R^4$ is chlorine substituted at the 6-position, $R^3$ and $R^5$ are hydrogens and A is sulphur.

10. A thioxathene derivative of the formula:

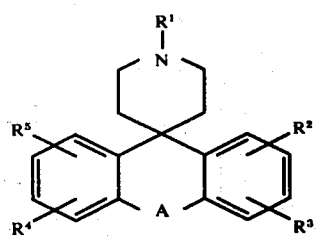

wherein $R^1$ is methyl, $R^2$ is acetoxy substituted at the 4-position, $R^3$, $R^4$ and $R^5$ are hydrogens and A is sulphinyl.

* * * * *